United States Patent [19]

Vallana et al.

[11] Patent Number: 5,084,151
[45] Date of Patent: Jan. 28, 1992

[54] METHOD AND APPARATUS FOR FORMING PROSTHETIC DEVICE HAVING A BIOCOMPATIBLE CARBON FILM THEREON

[75] Inventors: Franco Vallana; Pietro Arru, both of Turin, Italy

[73] Assignee: Sorin Biomedica S.p.A., Vercelli, Italy

[21] Appl. No.: 480,094

[22] Filed: Feb. 14, 1990

Related U.S. Application Data

[60] Division of Ser. No. 464,629, Jan. 3, 1990, which is a continuation of Ser. No. 391,658, Aug. 8, 1989, abandoned, which is a continuation of Ser. No. 80,205, Jul. 22, 1987, abandoned, which is a continuation-in-part of Ser. No. 801,753, Nov. 26, 1985, abandoned, which is a continuation of Ser. No. 799,561, Nov. 20, 1985, abandoned, which is a continuation of Ser. No. 545,292, Oct. 25, 1983, abandoned.

[51] Int. Cl.⁵ .................................................. C23C 14/34
[52] U.S. Cl. .......................... 204/192.11; 204/192.14; 204/192.15; 204/298.04; 204/298.09; 204/298.15; 204/298.28
[58] Field of Search ............ 204/192.11, 192.14, 204/192.15, 192.38, 298.04, 298.06, 298.09, 298.27, 298.28, 298.29, 298.41, 192.16, 298.15

[56] References Cited

U.S. PATENT DOCUMENTS

| | | | |
|---|---|---|---|
| 3,399,969 | 9/1968 | Bokros et al. | 21/209.1 |
| 3,472,751 | 10/1969 | King | 204/192.11 |
| 3,526,005 | 9/1970 | Bokros et al. | 3/1 |
| 3,546,711 | 12/1970 | Bokros | 3/1 |
| 3,547,676 | 12/1970 | Bokros et al. | 117/46 |
| 3,579,645 | 5/1971 | Bokros | 3/1 |
| 3,623,164 | 11/1971 | Bokros | 3/1 |
| 3,676,179 | 7/1972 | Bokros | 117/46 |
| 3,677,795 | 7/1972 | Bokros et al. | 117/46 |
| 3,685,059 | 8/1972 | Bokros et al. | 3/1 |
| 3,707,006 | 12/1972 | Bokros et al. | 3/1 |
| 3,722,004 | 3/1973 | Cromie | 3/1 |
| 3,737,919 | 6/1973 | Child | 3/1 |
| 3,738,906 | 6/1973 | Olcott | 161/168 |
| 3,783,868 | 1/1974 | Bokros | 128/260 |
| 3,825,956 | 7/1974 | Child | 3/1 |
| 3,835,475 | 9/1974 | Child | 3/1 |
| 3,839,182 | 10/1974 | Sager | 204/192.38 X |
| 3,840,451 | 10/1974 | Golyanov et al. | 204/192 |
| 3,877,080 | 4/1975 | Olcott | 3/1 |
| 3,901,808 | 8/1975 | Bokros | 210/263 |
| 3,907,660 | 9/1975 | Gillery | 204/298 |
| 3,924,034 | 12/1975 | Olcott | 427/228 |
| 3,952,334 | 4/1976 | Bokros et al. | 3/1 |
| 3,969,130 | 7/1976 | Bokros | 117/332 |
| 3,971,134 | 7/1976 | Bokros | 32/10 A |
| 3,972,818 | 8/1976 | Bokros | 210/435 |
| 3,977,896 | 8/1976 | Bokros | 427/213 |
| 3,977,923 | 12/1976 | Possis | 3/1.5 |

(List continued on next page.)

FOREIGN PATENT DOCUMENTS 0029787 3/1981 European Pat. Off. .

(List continued on next page.)

OTHER PUBLICATIONS

Aisenberg et al., "Ion-Beam . . . Carbon", J. of Appl. Phys., vol. 42, No. 7, 6/71, pp. 2953-2958.

(List continued on next page.)

*Primary Examiner*—Nam X. Nguyen
*Attorney, Agent, or Firm*—Shea & Gould

[57] ABSTRACT

A prosthetic device which includes a biocompatible carbon film firmly adherent to a substrate. The carbon preferably is turbostratic and is preferably very thin, e.g., less than about one micron. The thin carbon biocompatible film is dense and covers at least that portion of the substrate which will be in contact with body tissue and/or fluids to insure against physiological rejection and degradation of the prosthetic device. The carbon can be deposited on a variety of substrates, including low temperature substrates, in situ, without adversely affecting the mechanical properties of the substrate. The prosthetic device of the invention is formed by triode sputtering vacuum deposition at a relatively low temperature to achieve the desired results with respect to the deposited carbon and the substrate and with respect to the required adherence therebetween.

20 Claims, 8 Drawing Sheets

U.S. PATENT DOCUMENTS

| | | |
|---|---|---|
| 4,015,601 | 4/1977 | Bokros et al. ............ 128/214 R |
| 4,029,844 | 6/1977 | Olcott .......................... 428/367 |
| 4,038,703 | 8/1977 | Bokros ............................ 3/1.5 |
| 4,092,983 | 6/1978 | Slivenko ................... 128/214 R |
| 4,108,173 | 8/1978 | Slivenko et al. ........ 128/214 R |
| 4,108,174 | 8/1978 | Slivenko ................... 128/214 R |
| 4,126,924 | 11/1978 | Akins et al. ................. 29/423 |
| 4,131,957 | 1/1979 | Bokros .......................... 3/1.91 |
| 4,142,958 | 3/1979 | Wei et al. ................ 204/192.11 |
| 4,149,277 | 4/1979 | Bokros .............................. 3/1 |
| 4,164,045 | 8/1979 | Bokros et al. ................. 3/1.4 |
| 4,166,292 | 9/1979 | Bokros .......................... 3/1.91 |
| 4,169,477 | 10/1979 | Bokros .......................... 128/334 |
| 4,173,522 | 11/1979 | Puler ............................ 204/192 |
| 4,194,028 | 3/1980 | Sirtl et al. ..................... 427/249 |
| 4,197,593 | 4/1980 | Kaster et al. ................... 3/1.5 |
| 4,204,542 | 5/1980 | Bokros et al. ............ 128/335.5 |
| 4,254,159 | 3/1981 | Palker et al. .......... 204/192.38 X |
| 4,254,508 | 3/1981 | Bokros ............................ 3/1.5 |
| 4,272,854 | 6/1981 | Bokros ............................ 3/1.5 |
| 4,274,437 | 6/1981 | Watts ............................ 137/527 |
| 4,276,658 | 7/1981 | Hanson et al. ................ 3/1.5 |
| 4,300,244 | 11/1981 | Bokros ............................ 3/1.4 |
| 4,300,245 | 11/1981 | Saunders ........................ 3/18 |
| 4,308,624 | 1/1982 | Klawitter ........................ 3/1.5 |
| 4,319,364 | 3/1982 | Kaster ............................ 3/1.5 |
| 4,325,373 | 4/1982 | Slivenko et al. ......... 128/303 R |
| 4,326,304 | 4/1982 | Klawitter ........................ 3/1.5 |
| 4,326,305 | 4/1982 | Davidas .......................... 3/1.9 |
| 4,328,592 | 5/1982 | Klawitter ........................ 3/1.5 |
| 4,349,498 | 9/1982 | Ellis et al. ..................... 264/81 |
| 4,376,688 | 3/1983 | Ceasar et al. ........ 204/192.31 X |
| 4,421,507 | 12/1983 | Bokros .......................... 604/52 |
| 4,443,894 | 4/1984 | Klawitter ........................ 3/1.5 |
| 4,451,937 | 6/1984 | Klawitter ........................ 3/1.5 |
| 4,474,556 | 10/1984 | Ellis et al. ..................... 433/173 |
| 4,486,286 | 12/1984 | Lewin ............................ 204/192 |
| 4,534,761 | 8/1985 | Raible .......................... 604/175 |
| 4,535,483 | 8/1985 | Klawitter et al. ............. 623/2 |
| 4,537,791 | 8/1985 | Tarjan ............................ 427/2 |
| 4,546,012 | 10/1985 | Brooks .......................... 427/213 |
| 4,594,270 | 6/1986 | Brooks .......................... 427/213 |
| 4,608,051 | 8/1986 | Reck et al. ..................... 623/10 |
| 4,624,822 | 11/1986 | Arru et al. ..................... 264/544 |
| 4,666,442 | 5/1987 | Arru et al. ..................... 264/544 |
| 4,793,908 | 12/1988 | Scott et al. ............. 204/192.11 X |

FOREIGN PATENT DOCUMENTS

| | | |
|---|---|---|
| 2020804 | 4/1970 | Fed. Rep. of Germany . |
| 3116040 | 11/1982 | Fed. Rep. of Germany . |
| 2364273 | 7/1978 | France . |
| 2399237 | 2/1979 | France . |
| 631743 | 8/1982 | Switzerland . |
| 641063 | 2/1984 | Switzerland . |
| 1165698 | 10/1969 | United Kingdom . |

OTHER PUBLICATIONS

C. Weissmantel, "Ion Beam . . . Structures", J. Vac. Sciene. Technol., 18(2), 3/81, pp. 179–185.

Banks et al., "Ion Beam . . . Films", J. Vac. Sci. Technol., vol. 21, No. 3, Sep./Oct. 1982, pp. 807–814.

J. Appl. Chem., vol. 6, pp 477–481, G. E. Bacon, 11/56.

The Handbook of Thin Film Technology, L. I. Maissel et al., 1970.

J. Biomed. Mater. Res. Symposium, No. 2 (Part 1), pp. 41–47, Jim Benson, 1971.

J. Vac. Sci. Technol., vol. 12, No. 5, pp. 1058–1066, T. C. Tisone et al., 1975.

Antithrombogenicity of Pyrolytic Carbon, pp. 57–60, H. Brauner et al., 1976.

Conferences on Carbon, vol. 13, pp. 338–339, N. K. Agarwal et al., 1977.

Trans. Am. Cos. Artif. Intern. Organs, W. V. Sharp et al., 1978.

Journal of Biomedical Materials Research, vol. 14, 145–154, Harvey S. Borovetz et al., 1980.

Pyrolite, Intermedics Orthopedics, 1982.

Biomat. Med. Dev. Art. Org., 10(3), pp. 187–203, Harvey S. Borovetz et al., 1982.

Blood/Carbon Interactions, pp. 88–92, Dr. Axel D. Haubold, 4/83.

Pyrolytic Graphite, pp. 139–195, William H. Smith et al., (pub. date unknown).

Biolite, Intermedics Orthopedics (pub. date unknown).

Pyrolytic Carbon-Coated Grafts, pp. 203–212, William V. Sharp et al (publ. date unknown).

Catalog, pp. 1–8, Balzers Aktiengeselschaft (publ. date unknown).

(List continued on next page.)

OTHER PUBLICATIONS

R. Yamada et al., "Measurement of Chemical Sputtering Yields of Various Types of Carbon", *Journal of Nuclear Materials*, 95 (1980), 278-284.

A. D. Haubold et al., "Biocompatibility of Clinical Implant Material", vol. II (1981).

J. Kakinoki et al., "Electron Diffraction Study of Evaporated Carbon Films", *Acta Cryst.*, (1960), 13, 171.

CarbonMedics Inc. Publication, date unknown, 4 pages.

Miramed S.p.A. Label, 1 page.

Meadox Medicals, Inc., Microvel Double Velour Graft, 2 pages.

Meadox Medicals, Inc., Cooley Double Velour Graft, 4 pages.

Meadox Medicals, Inc., Meadox Dardik Biograft, 2 pages.

C. H. Myer et al., "Development of Carbon Film Composites for Use in Prosthetic Devices".

N. K. Agarwal et al., "Vacuum-Deposited Carbon Coatings", Thin Solid Films, vol. 40 (1977), pp. 299-308.

Z. Marinkovic et al., "Preparation and Properties of Sputtered 'Glassy' Carbon Films", Carbon, vol. 14 (1976), pp. 329-331.

J. C. Bokros, "Carbon Biomedical Devices", Carbon, vol. 15 (1977), pp. 355-371.

H. S. Shim et al., "The Wear Behavior of Vacuum-Vapor-Deposited Carbon Films," Journal of Bioengineering, vol. 2 (1973), pp. 341-343.

H. S. Borovetz et al., "Scanning Electron Microscopic and Surface Analytical Study of an Isotropic Vapor Deposited Carbon Film on Microporous Membrane," Scanning Electron Microscopy, vol. II, 1978, pp. 85-94.

J. N. Kent et al., "Pyrolytic Carbon and Carbon-Coated Metallic Dental Implants," Dental Clinics in North America, vol. 24 (1980), pp. 465-485.

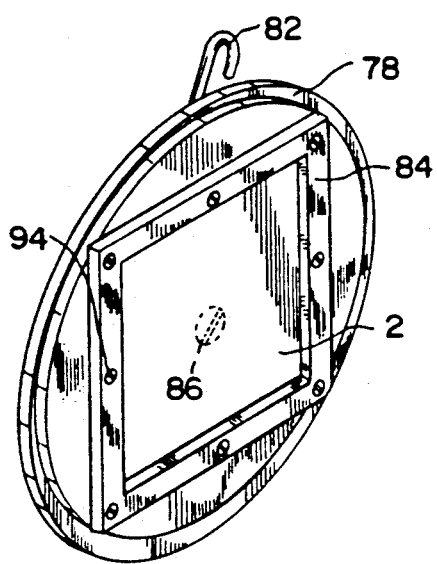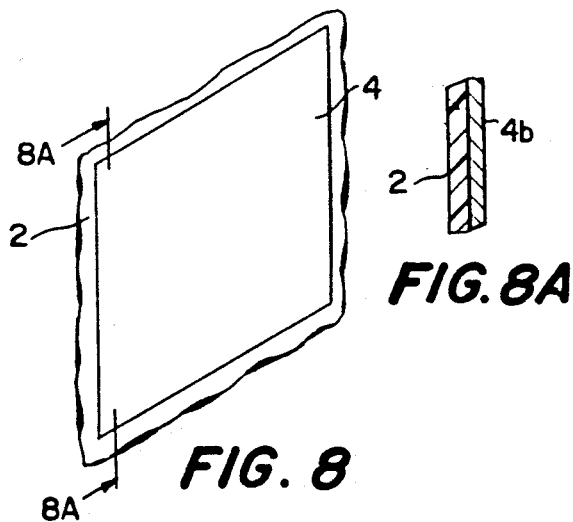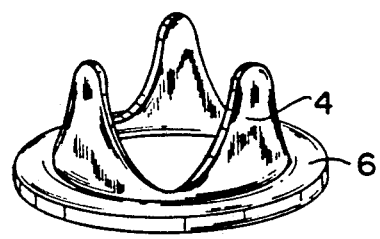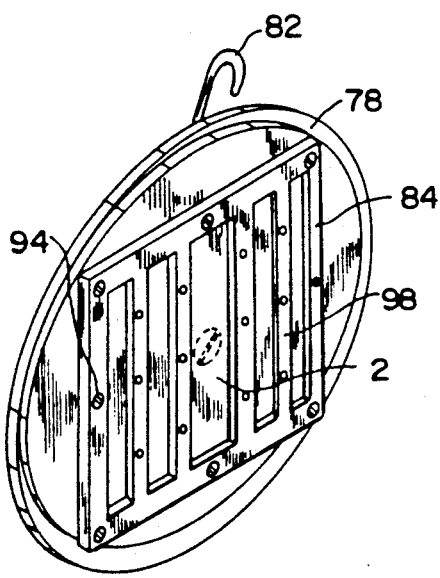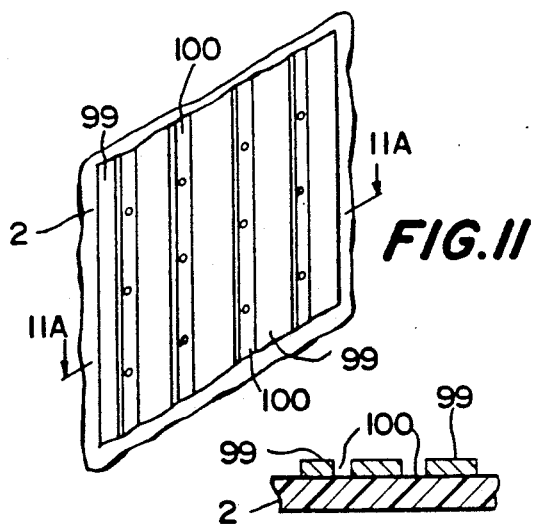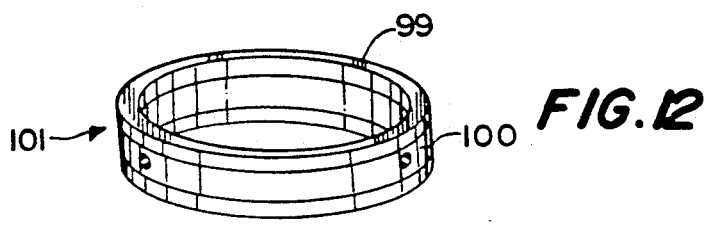

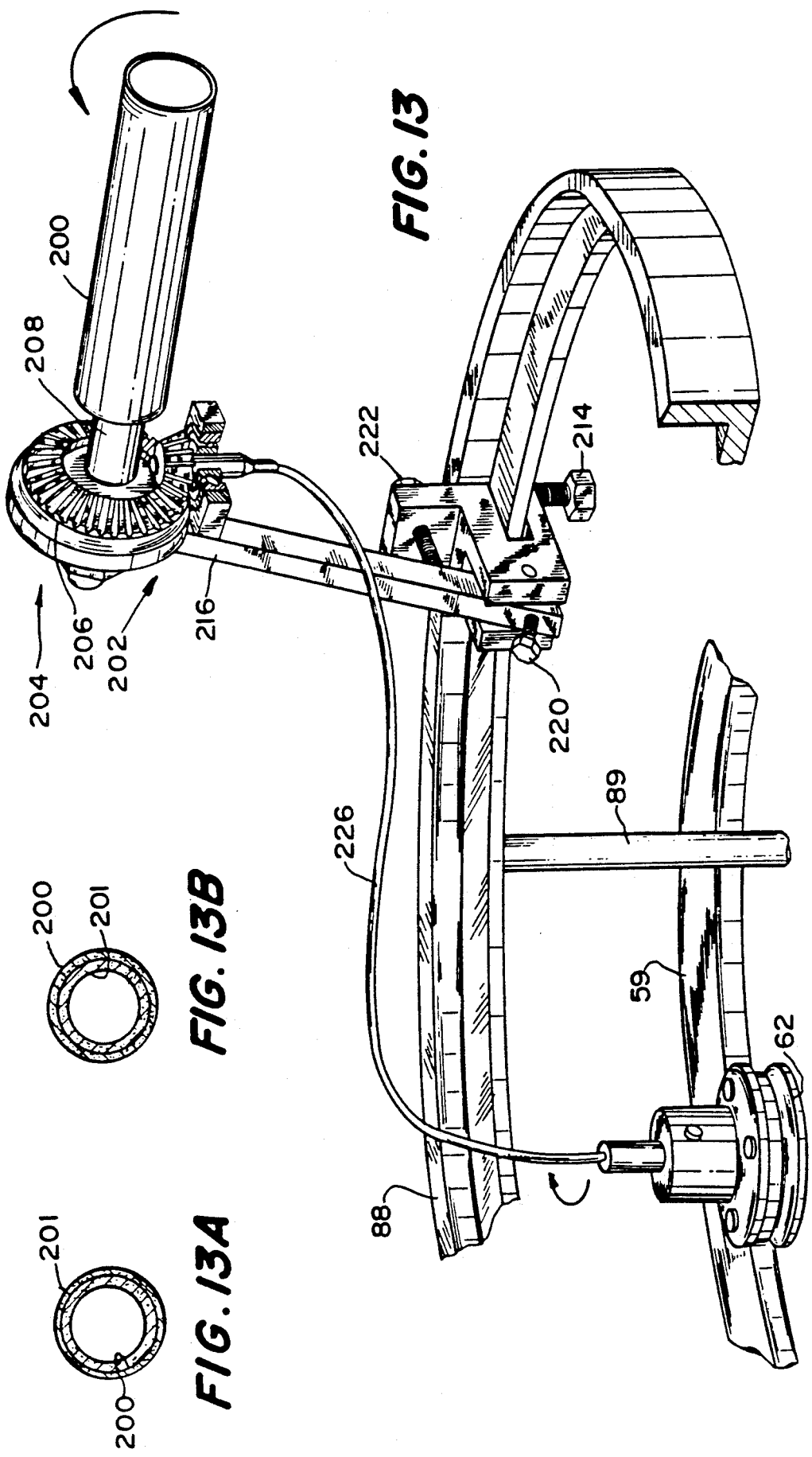

METHOD AND APPARATUS FOR FORMING PROSTHETIC DEVICE HAVING A BIOCOMPATIBLE CARBON FILM THEREON

This is a divisional of application Ser. No. 07/464,629 filed Jan. 3, 1990, which is a continuation of Ser. No. 07/391,658 filed Aug. 8, 1989 (now abandoned); which is a continuation of Ser. No. 07/080,205 filed July 22, 1987 (now abandoned); which is a continuation-in-part of Ser. No. 06/801,753 filed Nov. 26, 1985 (now abandoned); which is a continuation of Ser. No. 06/799,561 filed Nov. 20, 1985 (now abandoned); which is a continuation of Ser. No. 06/545,292 filed Oct. 25, 1983 (now abandoned).

This application is a continuation-in-part application of Ser. No. 545,292, filed Oct. 25, 1983.

FIELD OF THE INVENTION

The invention relates to a prosthetic device having a thin continuous biocompatible film of carbon firmly adherent to a substrate, and to a method of and apparatus for forming the prosthetic device.

BACKGROUND OF THE INVENTION

Prior to the present invention, a satisfactory prosthetic device having a thin continuous film of biocompatible carbon firmly adherent to a substrate has not been generally available. Existing carbon films have not exhibited adherence to their substrate or have not been in a form which is biocompatible. Another deficiency of prior art carbon coated prosthetic devices is that the mechanical properties of the substrates have been adversely affected by the methods and apparatus employed to form the films thereon.

Representative of the prior art techniques for coating a carbon film on a substrate of a prosthetic device include chemical vapor deposition, thermal evaporation by means of an electron beam and ion plating.

In early chemical vapor deposition techniques for forming prosthetic devices, a source for carbon was decomposed at relatively high temperatures and the carbon was deposited in thick layers (e.g., at least 25 microns) on a substrate (see, for example, U.S. Pat. Nos. 3,526,005; 3,685,059 and 3,707,006). Since these techniques typically employed high temperatures e.g., in excess of 1000° C., it was necessary to select substrate materials which were not adversely affected by the high temperatures employed during the process. As a result, the substrate materials employed for the making of prosthetic devices were limited. To this day, such high temperature techniques cannot take advantage of the desirable properties of available low temperature substrate materials.

Efforts to overcome drawbacks attendant to high temperatures have included initially coating the substrates with high temperature organic polymers and then depositing the carbon thereon (see, for example, U.S. Pat. No. 3,952,334). Such techniques are relatively complex and have not met with significant success.

The described prior art techniques also have been relatively costly and have produced a layer of carbon which has not satisfactorily adhered to the substrate. In use it has been found that the carbon layer tends to separate from the substrate and allows body fluids and tissue to attack and degrade the prosthetic device.

Attempts to modify existing chemical vaporization techniques continue. Recently, it has been suggested that catalysts be used to lower processing temperatures. However, such suggestions add to the complexity and costs of the process and result in films which, in use, have experienced undesirable degradation and separation from the substrates intended to be protected.

Other techniques which have been tried and which have not met with success include electron beam evaporation and ion plating of carbon on a substrate. It has been found that the infrared radiation generated by the electron beam evaporation technique causes degradation of the substrate. In addition, the pressures used are so low that the carbon atoms tend to flow in a very straight line and do not uniformly coat a substrate which normally has a morphologically complex surface.

Further, with the electron beam technique, the deposited carbon is not biocompatible and does not firmly adhere to the substrate. The carbon on the substrate is in form of graphite which has been found not to be biocompatible. Also, the deposited carbon tends to separate and is removed from the substrate during use causing body fluids and tissue to attack and degrade the prosthetic device.

With respect to the ion plating technique, it is a modification of vacuum evaporation in which the substrate is held during the deposition at a high negative potential so that it is bombarded by positive ions, in order to improve the adhesion and the structural properties of the film. Obviously this technique cannot be advantageously employed with electrically insulated substrates, like polymers. In fact, it is difficult to electrically bias non-conductive desirable substrates, such as DACRON (a polyester resin), TEFLON (polytetrafluoroethylene) and other relatively low melting polymers.

Thus, available prosthetic devices and techniques are beset by drawbacks. There is a need for prosthetic devices which have a thin biocompatible carbon coating firmly adherent to the substrate, such as low temperature DACRON and TEFLON, etc., and which are relatively simple and inexpensive to produce.

SUMMARY OF THE INVENTION

In accordance with the present invention, there is provided a new and unique prosthetic device which includes a biocompatible carbon film firmly adherent to a substrate. The carbon preferably is turbostratic and is preferably very thin, e.g., less than about one micron. The thin carbon biocompatible film is dense and covers at least that portion of the substrate which will be in contact with body tissue and/or fluids to insure against physiological rejection and degradation of the prosthetic device. The carbon can be deposited on a variety of substrates, including low temperature substrates, in situ, without adversely affecting the mechanical properties of the substrate. The preferred substrates include fabrics of medical grade DACRON and TEFLON which have relatively low softening points, and non-refractory metals, such as Haynes 25 alloy.

The prosthetic devices of the present invention include valves, particularly cardiac valves, grafts and patches, including vascular grafts, tubular prostheses, sutures, catheters, otologic prostheses, tendon and ligament prostheses, dental implants, jaw replacements and other prosthetic devices for the repair or replacement of bones and joints.

Also in accordance with the present invention, there is provided a new and unique method of and apparatus for forming the prosthetic devices of the present invention, wherein the carbon is deposited on the substrate, in situ, at a low temperature and pressure and in a manner which enhances the adhesion of the carbon and does nor adversely affect the properties of the substrate.

Preferably the prosthetic devices of the invention are formed by triode sputtering vacuum deposition which achieves the desired results with respect to the carbon and the substrate and the required adherence therebetween. In the triode sputtering vacuum deposition of the present invention there is provided an upper and remote ionization chamber for generating a plasma beam of an inert gas containing positively charged ions of high energy, a lower sputtering chamber, including a carbon source (target) spaced from the ionization chamber which is negatively charged and surrounded by an anode, an intermediate magnetic coil about the sputtering chamber for collimating the plasma beam, and a substrate of the prosthetic device positioned within the sputtering chamber and in proximity to the target for receiving the carbon atoms sputtered from the target by the bombarding ions of the plasma beam.

In the present invention, the ionization of the inert gas and generation of plasma is achieved in an ionization chamber which is remote from the target. Since the substrate is in relative proximity to the target, and remote from the ionization chamber, the substrate is insulated from the high temperatures used to generate the plasma. Accordingly, the present invention minimizes transfer of heat to the substrate.

Additionally, means are provided for cooling the target and the anode which further serves to minimize the transfer of heat to the substrate.

Furthermore, the present invention employs a high voltage, low current (preferably direct current) to the target (carbon cathode) which further reduces the heat generated in the lower sputtering chamber.

Another feature of the invention is to operate the sputtering chamber at low pressures so that the force and speed of the sputtered carbon is not deterred by its environment.

Thus, the present invention operates at low temperatures and pressures so that the substrates are not adversely affected and the sputtered carbon firmly adheres thereto.

Another feature of the present invention is that either graphite or pyrolytic carbon can be used for the target. In either instance, the carbon deposited on the substrate is a biocompatible carbon which is turbostratic in structure.

Another feature is that regardless of the configuration of the substrate, e.g., flat or curved, the invention produces a thin, uniform, dense film of turbostratic carbon thereon. This is accomplished by movably positioning the substrates within the sputtering chamber to insure uniform deposition of carbon.

Still another feature of the present invention is that specific temperature gradients can be used at the substrates to improve adherence of the biocompatible carbon being deposited thereon.

In each embodiment of the invention there is obtained the desired prosthetic device including a biocompatible film of turbostratic carbon of the desired thinness and uniformity, deposited on and firmly adherent to a substrate so that the device has and maintains its integrity.

BRIEF DESCRIPTION OF THE DRAWINGS

The following is a detailed description together with accompanying drawings of illustrative embodiments of the invention. It is to be understood that the invention is capable of modification and variation apparent to those skilled in the art within the spirit and scope of the invention.

FIG. 7 is a perspective view of a disk and frame for holding a substrate which is to be coated in accordance with the present invention;

FIG. 8 is a perspective view of the coated substrate of the invention after it has been removed from the disk and frame shown in FIG. 7;

FIG. 8A is a cross sectional view of the coated substrate of FIG. 8;

FIG. 9 is a schematic view of a component for a cardiac valve encased within the coated substrate of FIG. 8;

FIGS. 10, 11, 11A and 12 are similar to FIGS. 7, 8, 8A and 9, but illustrate the use of a disk and frame (FIG. 10) for coating a masked substrate which allows the substrate to be coated only over selected portions (FIG. 11 and 11A) for use in a ring of a mechanical cardiac valve (FIG. 12);

FIG. 13 is a perspective view of an apparatus of the invention for coating tubing, e.g., vascular tubing, which can be positioned in the apparatus of FIGS. 1-5;

FIG. 13A is a cross sectional view of the coated tubing prior to inversion;

FIG. 13B is a cross sectional view of the coated tubing after inversion;

Referring first to the illustrative embodiments of the invention of FIGS. 1-9, there is shown a triode vacuum apparatus 10 (FIGS. 1-7) for coating a substrate 2 with a thin, uniform, dense coating or film 4 of biocompatible carbon firmly adherent to the substrate 2 (FIGS. 8 and 8A) for use in a prosthetic device 6 (FIG. 9).

Figure 3:
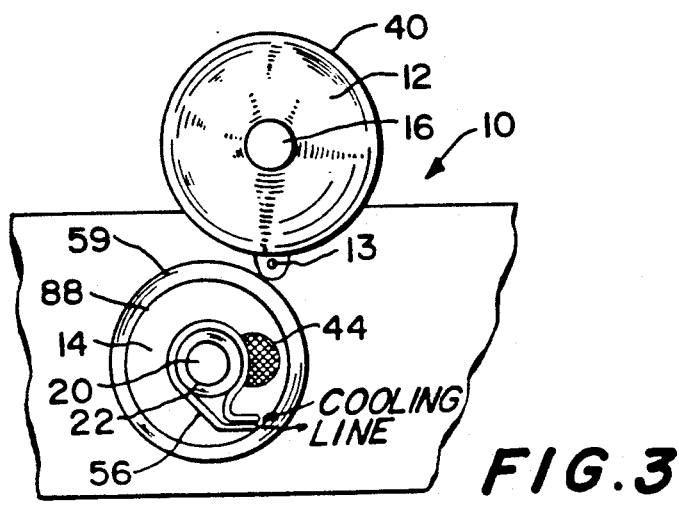
FIG. 3 is a top view of the apparatus of FIG. 1, wherein the bell jar has been rotated out of the way for purpose of loading substrates to be coated and for removing coated substrates.
Figure 4:
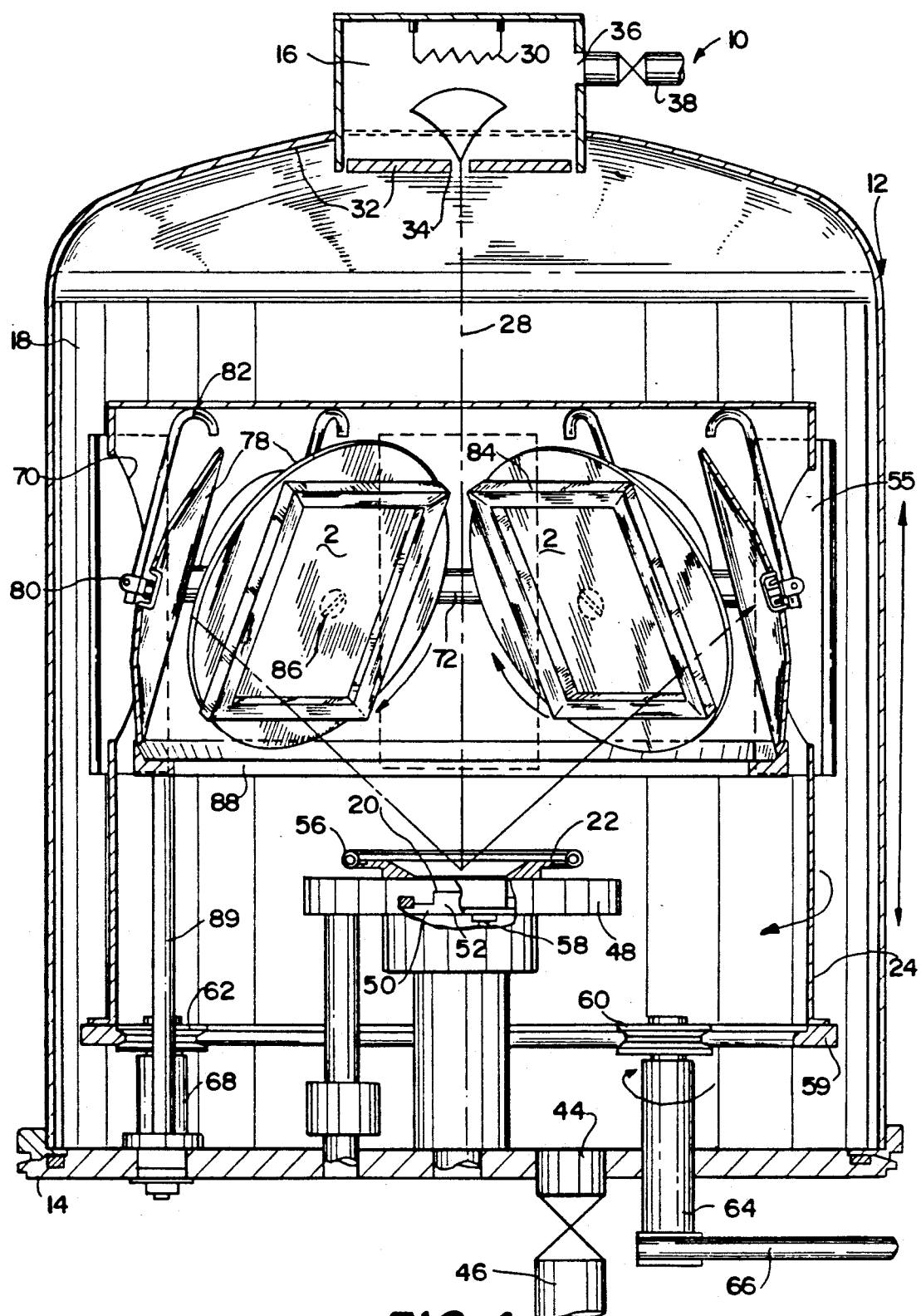
FIG. 4 is a longitudinal sectional view of the sputtering apparatus of FIGS. 1-3, illustrating the ionization and sputtering chambers, the target and anode, and an internal housing including disks for holding the substrates to be coated.

The apparatus 10 (FIGS. 1-6) includes a bell jar 12 mounted on a hydraulically operated telescoping arm 13 for moving the jar 12 to and from a base 14. The bell jar 12 has an upper ionization chamber 16 and a lower sputtering chamber 18. Positioned in the sputtering chamber 18 when the jar 12 is closed (FIGS. 1 and 4) is a target 20 which provides a source for the biocompatible carbon and which is circumscribed by an anode 22. Also within the closed sputtering chamber 18 is a removable support structure or housing 24 for the substrates 2 to be coated by the carbon (FIG. 4). This illustrative apparatus is of the general type marketed by Balzers AG of Liechtenstein under Model BB 800 033 PE 7503.

The ionization chamber 16 generates a plasma beam 28 (FIGS. 1 and 6) of concentrated ionized particles which are drawn to the target 20 for sputtering carbon onto the substrates 2. The chamber 16 includes a filament 30 at its upper end, an auxiliary anode 32 at its lower end having a central opening 34 therethrough and an intermediate inlet 36 for an inert gas, such as argon, which forms the plasma beam 28. The argon gas flows from a source (FIG. 6) through a valve controlled conduit 38 connected to the inlet 36 and into the ionization chamber 16, wherein the heated filament 30 ionizes the argon into concentrated positively charged ions which are drawn through the opening 34 of the auxiliary anode 32 into sputtering chamber 18 to the target 20. As the argon ions are drawn through the sputtering chamber 18 they are collimated into the shape schematically illustrated in FIG. 6 by a magnetic field coil 40 centrally positioned about the outer wall of the sputtering chamber 18. As desired gases in the sputtering chamber 18 can be removed by a vacuum pump connected to a vacuum outlet 44 in the base 14 via the valve controlled conduit 46 (FIGS. 3 and 4). Throughout the operation the vacuum pump maintains the sputtering chamber 18 at low pressures so that the environmental effect on the force and speed of the sputtered carbon is minimal.

As illustrated in FIG. 4, the target 20 and the substrates 2 are spaced from the ionization chamber 16. Accordingly the heat generated in forming the plasma beam 28, in substance, does not reach or adversely affect the substrates 2.

Figure 2:
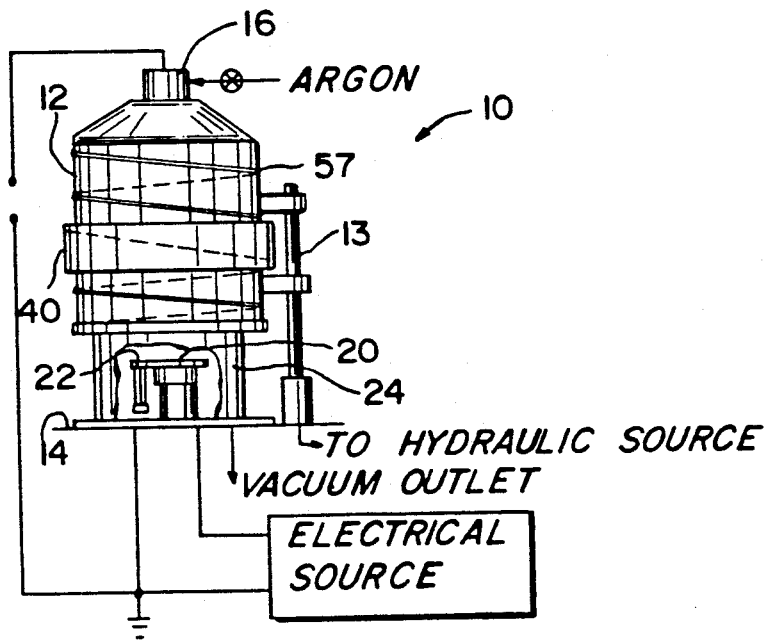
FIG. 2 is a perspective view of the triode sputtering vacuum apparatus of FIG. 1 wherein the bell jar (ionization and sputtering chambers) is hydraulically raised from its base to expose the target and surrounding anode.
Figure 6:
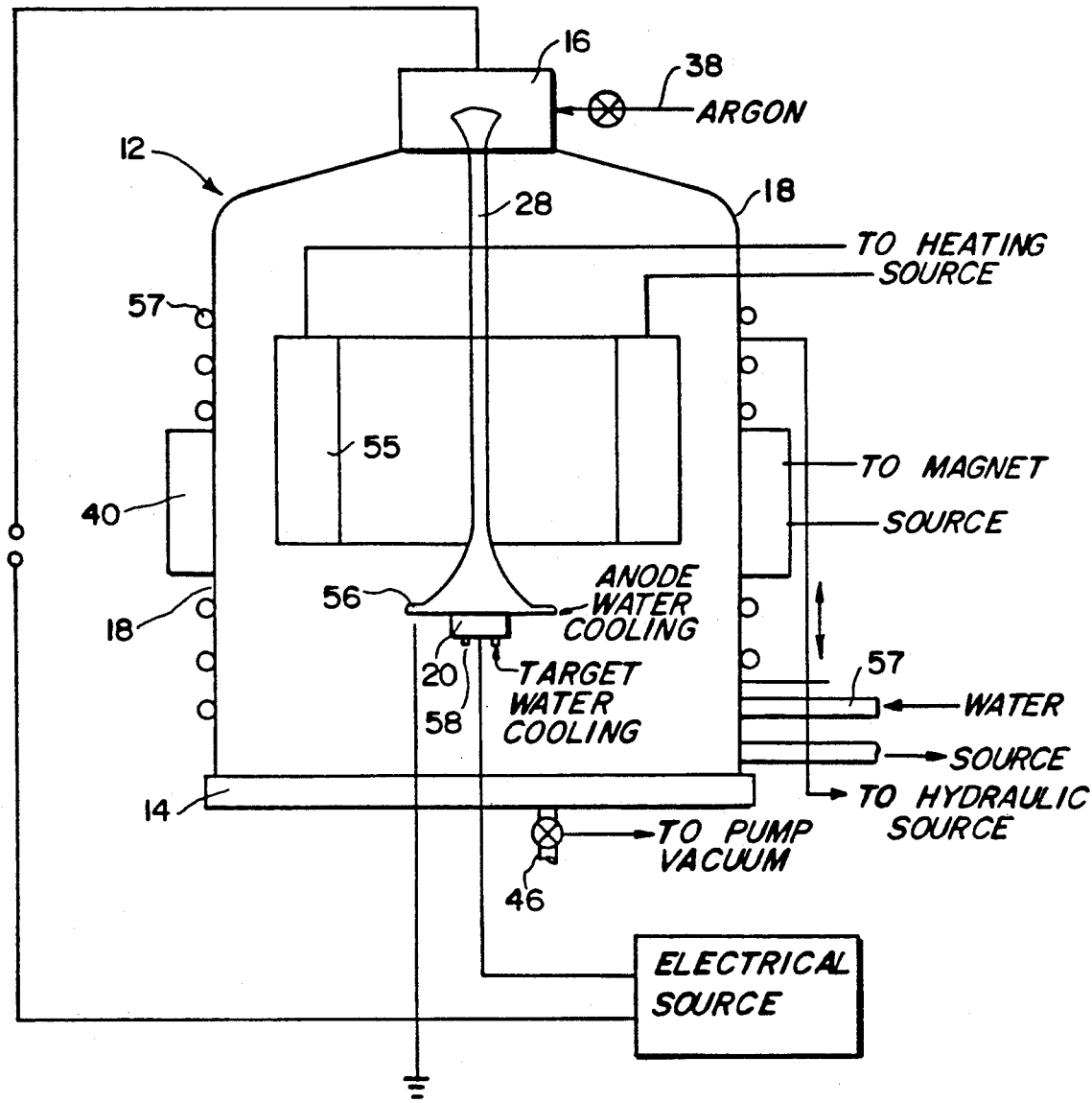
FIG. 6 is a schematic view of the apparatus of FIG. 1 illustrating the electric circuits and heating, cooling, hydraulic and vacuum systems utilized by the invention, along with showing the plasma beam generated in the ionization chamber centered and directed to the target area.

The target 20 and anode 22 are mounted within and on a stand 48 affixed to the base 14 (FIGS. 2, 4 and 6). The target 20 is positioned within a cylindrical cavity 50 and is circumscribed by the annular anode 22.

The target 20 can comprise graphite, pyrolytic carbon or a combination thereof. Surprisingly and unexpectedly in each embodiment the carbon sputtered onto the substrates 2 is in a biocompatible form, namely turbostratic. In the illustrative embodiment (FIG. 4), the target 20 is cylindrical and comprises a graphite base 52 upon which is positioned an outer layer 54 of pyrolytic carbon.

To produce the required adhesion of the deposited carbon without adversely affecting the substrate 2, high voltages and low currents are used for the target 20 by the electric source (FIG. 6). Also, the target 20 and anode 22 are water cooled. By so doing, heat from infrared radiation from the target 20 and anode 22 is minimized.

It has been found that the relatively high voltages, e.g., at least about 500 volts and preferably about 1000 to 3000 volts, provide the energy needed to properly adhere the sputtered carbon to the substrate and a suitable deposition rate, while low direct currents, e.g., about 0.05 to 0.3 amps., minimize infrared and ultraviolet radiation. On the other hand, low voltage levels adversely affect the adhesion of the carbon to the substrate without meaningfully changing the generation of infrared radiation and high currents produce infrared and ultraviolet radiation that can adversely affect the substrates 2.

It also has been found that circulating cooling water from a source through an annular conduit 56 contiguous with the outer perimeter of the anode 22 and an annular conduit 58 beneath the cavity wall and in contact with the target 20 minimizes the generation of detrimental heat.

To further control the environment within the bell jar 12 and to enhance coating of the substrates 2, there are provided electric quartz heaters 55 mounted on the inner wall of the sputtering chamber 18 and about the mounted substrates 2, and a conduit 57 helically wrapped about the periphery of the outer wall of the sputtering chamber 18 through which water can be conveyed. The use of the heaters 55 and the conduit 57 to enhance the operation of the apparatus 10 will be explained in detail hereinafter.

Figure 5:
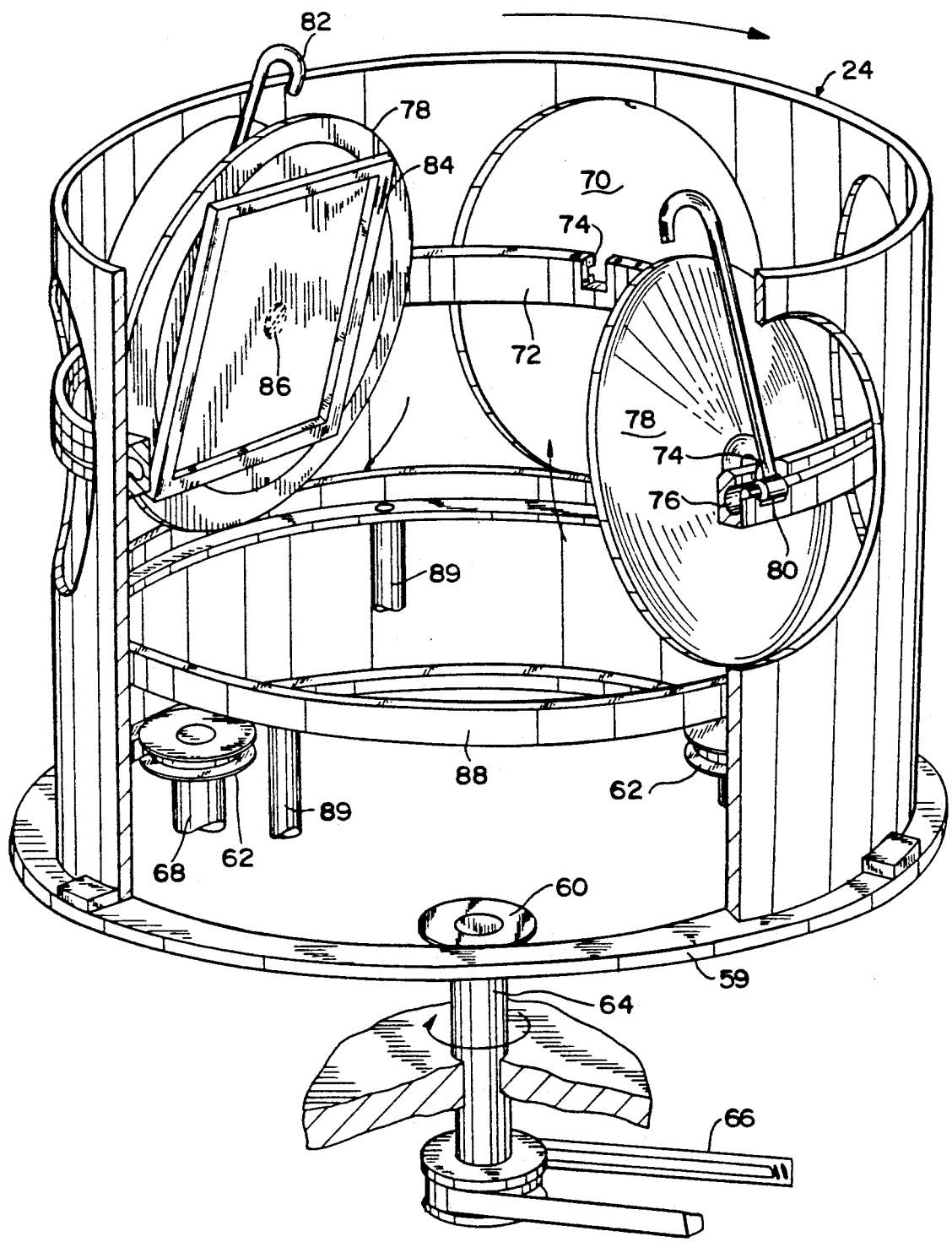
FIG. 5 is a perspective view of a lower rotatable ring of the apparatus of FIGS. 1-3, upon which the internal housing is placed, and an upper stationary ring for engaging and causing the disks to rotate about their centers as the housing and disks are rotated by the lower rotatable ring about the longitudinal axis of the bell jar.

Removably and rotatably positioned within the sputtering chamber 18 is the internal housing 24 for the substrates 2 (FIGS. 4 and 5). The housing 24 and related structure are designed to facilitate the coating of the substrates 2 with a dense thin film of turbostratic carbon from the sputtered target 20. As will be presently described, such structure positions the substrates 2 relative to the target 20 and simultaneously rotates such substrates 2 at predetermined rates about their axis and the longitudinal axis of the bell jar 12 to optimize uniform coating thereon.

More particularly, the housing 24 is cylindrical and is supported at its lower end on a rotatable cylindrical ring 59 driven by a belt driven roller 60 and supported by idler rollers 62. The roller 60 is connected to the upper end of a shaft 64 rotated by a belt 66 which is driven by a motor (not shown). The idler rolls 62 are connected to the upper ends of shafts 68 which are connected at their lower ends to the base 14.

The housing 24 extends upwardly from the lower rotable ring 59, about the target 20 and anode 22 and into the upper portion of the sputtering chamber 18. In the upper portion of the housing 24 there are six equal spaced circular openings 70. A cylindrical rail 72 is secured to the inner wall of the housing 24 and traverses the openings 70. In the rail 72, there is a notch 74 centrally positioned in each opening 70 for allowing access to an annular slot 76 in the rear wall of the rail 72.

The described structure of the housing 24 is adapted to receive disks 78 which hold the substrates 2. Each disk 78 has a shaft 80 centrally connected to its convex rear wall which is removably seated in the notch 74 and adjacent slot 76, and a hanger 82 extending upwardly therefrom to facilitate carrying, holding and storing of the disks 78. Each disk 78 also includes a frame 84 on its concave front wall which is secured to the disk 78 by a screw or other means 86 and which is used to hold the substrate 2.

Within the housing 24 and at the base of the openings 70 is a separate stationary ring 88 having rods 89 depending therefrom which are connected at their lower ends to the base 14. As illustrated in engaging the rail 72, the disks 78 tilt slightly forward with their lower ends frictionally engaging the stationary ring 88. As a consequence, when the housing 24 is rotated within the sputtering chamber 18, the disks 78 simultaneously rotate about their axis and the longitudinal axis of the bell jar 12 for uniform coating of the substrate 2. In addition, the disks 73 are tilted forwardly toward the target 20 and positioned a predetermined distance therefrom to optimize uniform coating of the sputtered carbon onto the rotating substrates 2.

The disks 78 can be used to secure a variety of substrates 2. Referring to FIGS. 7 through 9 a rectangular shaped substrate 2 is secured in a correspondingly shaped frame 84 on a disk 78 by screws or other means 94. After forming the biocompatible carbon film 4 on the substrate 2 in accordance with the present invention, the coated substrate 2 is removed from the frame 84 and can be wrapped around and secured to a stent of a cardiac valve, for example, to form the prosthetic device 6 shown in FIG. 9. In doing so, biocompatible carbon coated sutures, which are preferably also prepared in accordance with the present invention as hereinafter more particularly described, can be used.

Certain prosthetic devices require only portions of the substrate to be coated with a biocompatible carbon film. For example, cardiac valves may have only a portion of the valve exposed to physiological fluids, or it may be desirable to have portions of the prosthetic device attached by tissues after implantation. Those portions not exposed to tissues and fluids or portions which are desirably attached to tissues are masked prior to coating. In such instance the triode sputtering vacuum process of the invention will provide a carbon film only on the unmasked portions. More specifically, and as shown in FIG. 10, the frame 84 has masking segments 98 overlaying the substrate 2. As a result, the present invention will provide a substrate 2 including coated and uncoated portions 99 and 100 (FIGS. 11 and 11A) which can be used to form a ring 101 (FIG. 12) for a cardiac valve comprising a substrate 2 having coated and uncoated regions 99 and 100, respectively.

In addition to the valve components 6 and 101 just described, the present invention can be used for producing grafts and patches, tubular prostheses, sutures, catheters, otologic prostheses, tendon and ligament prostheses, dental implants, jaw replacements and other prosthetic devices. The prosthetic devices of the invention are especially useful as implants because they are biocompatible with body fluids and tissue. The implanted prosthetic devices of the invention resist physiological rejection and degradation. In each embodiment of the invention, the prosthetic device consists of or includes a substrate 2 with a thin, uniform, dense film or coating 4 and 99 of biocompatible carbon adherent thereto. See illustrative FIGS. 8A and 11A.

In the present invention, a wide variety of substrate materials can be used, however, the invention is particularly well suited for substrates comprising organic polymers having relatively low softening points. The substrates includes DACRON which exhibits a change in elasticity at about 150° C. Therefore, it is preferred when coating DACRON to have the substrate exposed to temperatures no higher than the range of 80°-90° C.

TEFLON is another suitable material which has low softening point substrate. TEFLON can withstand temperatures of about 250° C. before softening. It is preferred to limit the temperature in proximity of a TEFLON substrate to no more than about 160°-180° C.

Other low temperature materials which can be used for the substrate include silicone, polyacetal resins (DELRIN), polyurethane, low density polyethylene, and non-refractory metals, such as Haynes 25 cobalt-chromium alloys, titanium and titanium alloys.

The thickness of the substrates will vary depending on the form of and type of material. Substrates in the form of woven or knit fabrics, such as DACRON or TEFLON fabrics used in cardiac valves typically are from about 0.1 to 1.0 mm in thickness, and desirably 0.3 mm.

As stated, the carbon films or coatings of the invention deposited on the described substrates are biocompatible, continuous, uniform, dense and cover at least those portions of the substrates which are in contact with physiological fluids that can degrade uncoated substrates.

The carbon film preferably is thin within the range of about 0.2 to 0.8 micron. Films having a thickness exceeding the preferred range tend to separate from the substrate and/or take too long to produce. Films below the preferred thickness may not uniformly cover the substrate surface.

The carbon film of the invention is dense, e.g., 2.2 gm/cm$^3$, and preferably is turbostratic because this form of carbon is known to be biocompatible. The carbon film of the invention also strongly adheres to the substrate so that the coated substrate is able to repeatedly flex without separation of the film. The adhesion is tested in accordance with the ASTM 03359 standard procedure.

Figure 1:
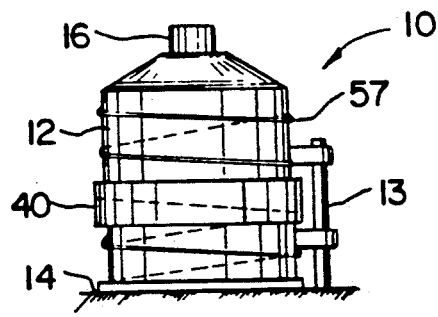
FIG. 1 is a perspective view of a preferred embodiment of a triode sputtering vacuum deposition apparatus for carrying out the present invention.

The process of the invention is admirably suited for forming the described biocompatible film on a wide variety of prosthetic devices consisting of or including coated substrates. To highlight the advantages of the invention, the following describes the process utilizing the illustrative embodiment of the apparatus 10 for forming the prosthetic device as shown in FIGS. 1 and 8, including low temperature substrates of medical grade DACRON and TEFLON.

Referring first to medical grade DACRON, the substrates 2 to be used are rectangular in shape as shown in FIG. 8. Prior to initiating the operational phase of the process, the DACRON substrates are cleansed by a non-corrosive solvent.

The cleansed substrates 2 are mounted by the frame 84 to the disks 78 (FIG. 9) and the loaded disks 78 are mounted on the rail 72 of the housing 24 (FIGS. 4 and 5). In so doing, the disks 78 tilt forward.

The bell jar 12 is raised from its base 14 by the hydraulically operated telescoping arm 13 and rotated on such arm 13 away from the base 14 as shown in FIG. 3. The housing 24 with the assembled disks 78 are placed on the lower rotatable ring 59 and the lower ends of the tilted disks 78 frictionally engage the stationary rail 88 positioned within the housing 24. The bell jar 12 is then rotated over the housing 24 and lowered by the hydraulically operated telescoping arm 13 about the housing 24 and into sealing engagement with the base 14 (FIGS. 2 and 1).

The sputtering chamber 18 is then evacuated and maintained at low pressure levels ($10^{-4}$ mbar–$10^{-2}$ mbar and preferably $10^{-3}$ mbar) by a vacuum pump via the outlet 44 and conduit 46. This is done to enhance the adhesion of the sputtered and the deposited carbon on the substrates 2. At such low pressure levels, the sputtered carbon atoms maintain their high energy level.

The target 20 is cleansed by bombardment of the plasma beam 28, and the bell jar 12 is cleansed by removal of moisture and gaseous impurities. The cleansing of the bell jar 12 is accomplished by feeding hot water through the helical conduit 57 about the wall of the sputtering chamber 18 and such chamber 18 is evacuated by a vacuum pump to remove vapors and gases.

Also to enhance adhesion of the sputtered carbon on the substrates 2, the temperature within the sputtering chamber 18 is maintained at about 80° C. by the use of the electric quartz lamps 55.

At the same time the filament 30 is operated at a current of about 80 to about 90 amperes, and preferably about 85 amperes, and argon gas is fed into the chamber 16 via conduit 38 and inlet 36, whereupon a plasma beam 28 is generated consisting of high energy positively charged ions. The plasma beam 28 is drawn from the ionization chamber 16 into the sputtering chamber 18 where it is focused or collimated by the magnetic field coil 40 and directed to the target 20. The coil 40 also serves to minimize exposure of the substrate 2 to secondary electrons. For such purposes, the coil 40 is operated at about 12 amperes.

The high energy argon ions of the plasma beam 28 bombard the target 20 causing carbon atoms to separate from the surface of the graphitic or pyrolytic target and flow in the acute angular direction schematically shown in FIG. 4 at substantial speeds onto the substrates 2. The substrates 2 are rotated about the longitudinal axis of the bell jar 12 and about their own axis to enhance uniform deposition of carbon. Typically, rotation about the jar 12 is at the rate of about 4 to 5 revolutions per minute while the disks 59 rotate about 2 revolutions about their axis for each revolution about the jar 12.

During operation, the target 20 is maintained at high voltages and low direct currents, such as 3000 volts and 0.3 amps, by the electric source. The high voltages help generate a suitable number of sputtered carbon atoms of the desired high energy while the low currents minimize the generation of infrared and ultraviolet radiation. Also, during operation the anode 22 and target 20 are cooled by water flowing at about 20° C. through their respective conduits 56 and 58 to minimize the generation of heat.

To further reduce the amount of undesirable heat at the substrate 2, the ionization chamber 16 is at the upper end of the sputtering chamber 18 and spaced a considerable distance from the substrate 2. In this illustrative example, the ionization chamber 16 is about 25 cm from the substrates 2.

The described process is continued until the carbon film 4 uniformly deposited on the DACRON substrates is about 0.3 microns in thickness. To achieve this thickness, the process is operated for about 5 hours.

After the desired thickness of biocompatible carbon film is obtained, the argon gas feed is shut off. After the pressure in the sputtering chamber 18 is raised to atmospheric pressure, the bell jar 12 is opened and the housing 24 is removed from the base 14. Thereafter, the disks 78 are removed from the housing 24 and the coated substrates 2 are removed from the frames 84.

The prosthetic devices thereby obtained include the desired carbon film 4 on the substrate 2 with the necessary adhesion therebetween and without adversely affecting the substrate.

In coating substrates 2 of TEFLON essentially the same process is employed. However, to obtain optimum adhesion of the carbon film 4, it has been found that a temperature gradient at the substrates 2 within the sputtering chamber 18 is desirable. With TEFLON substrates, the quartz electric lamps 55 are operated so as to heat the environment at the substrates 2 to about 180° C. until about one-sixth of the total desired thickness of the carbon film (0.3 microns) is deposited on the TEFLON substrates. Thereafter, heating of the substrate is terminated and the temperature in and about the substrates 2 is cooled down to and maintained at about 40° C. This is accomplished by shutting off the quartz electric lamps 55 and conveying cooling water through the helical conduit 57 about the outer wall of the sputtering chamber 18. Deposition of carbon to the full thickness of the deposited carbon was carried out under the same conditions already described, except that the anode current was reduced to about 0.1 amps. The operational time was about 8 hours.

The prosthetic devices obtained by the process produced the desired carbon films 4 on the TEFLON substrates 2 with the required adhesion therebetween and without adversely affecting the TEFLON.

Thus far there has been described, in some detail, the coating of flat substrates 2 for use in prosthetic devices. It is to be understood that the present invention can be used to provide biocompatible carbon films of a variety of prosthetic devices of different configurations, including tubular structures (e.g., vascular tubing and catheters) and yarns (e.g., sutures).

In FIG. 13, for example, vascular tubing 200 is coated with a carbon film 201 of the present invention (FIG. 13A). The illustrative apparatus 202 includes a drive assembly 204 comprising a gear mechanism 206 which rotates a spindle 208 having the tubular substrate 200 thereon. The drive assembly 204 is secured to the stationary rail 88 by a clamp 208 and bolt 214. A bar 216 of the assembly 204 is adjustably secured at one end to the clamp 210 by bolts 220 and 222 and at its other end to the gear mechanism 206.

The gear mechanism 206 is rotated by a rotable flexible cable 226 connected at one end to the gear mechanism 206 and its other end to the previously described idler roller. Rotation of the ring 59 by the drive roller 60 (FIG. 6) causes the idler roller 62 to rotate cable 226 which, in turn, rotates the gear mechanism 206. In so doing, the gear mechanism 206 rotates the spindle 208 and tubing 200 thereon.

In operation, the tubular substrate 200 is rotated during the sputtering process whereby sputtered carbon atoms from the target 20, as already described and illustrated (FIGS. 1–6), impinge on the tubular substrate 200 until a uniform thin biocompatible carbon film 201 is obtained. If desired the coated exterior surface of the tubing 200 can be inverted by inserting the tubing within itself to provide an inert coated interior surface. Also, this technique can be used for coating both surfaces of the tubing 200 by simply remounting the inverted tubing 200 on the spindle 208 and repeating the process to coat its "new" uncoated exterior surface.

In accordance with the described process tubing of DACRON was coated with the biocompatible carbon film 201 of the invention by rotating the tubing 200 about 5 revolutions per minute in about 9 hours under conditions similar to the described conditions for coating the substrate 2 of DACRON.

Biocompatible carbon coated yarns, such as sutures, also can be produced in accordance with the present invention.

Figure 14:
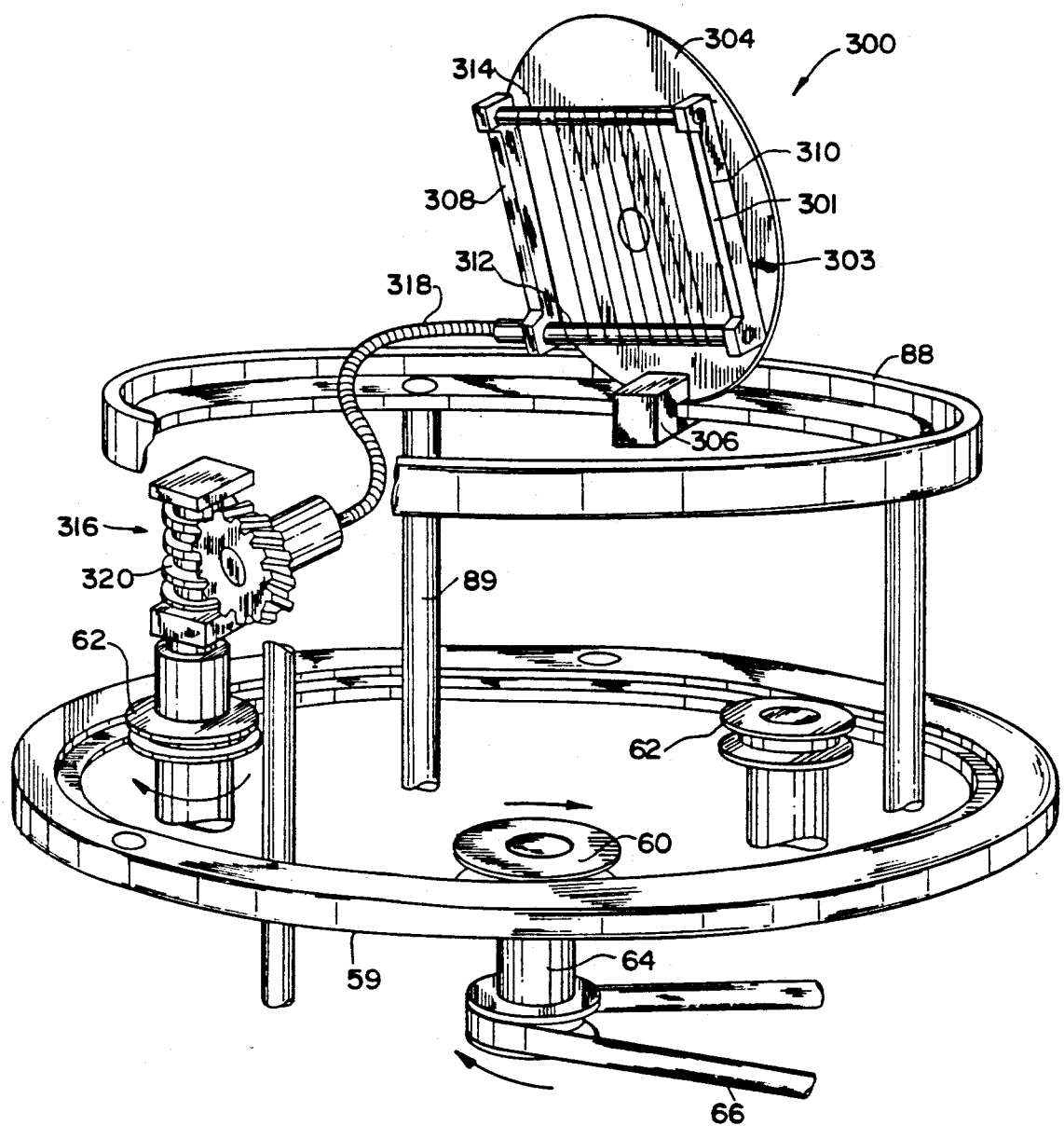
FIG. 14 is a perspective view of another apparatus of the invention for coating suture yarn which also can be positioned in the device of FIGS. 1-5.
Figures 15, 16:
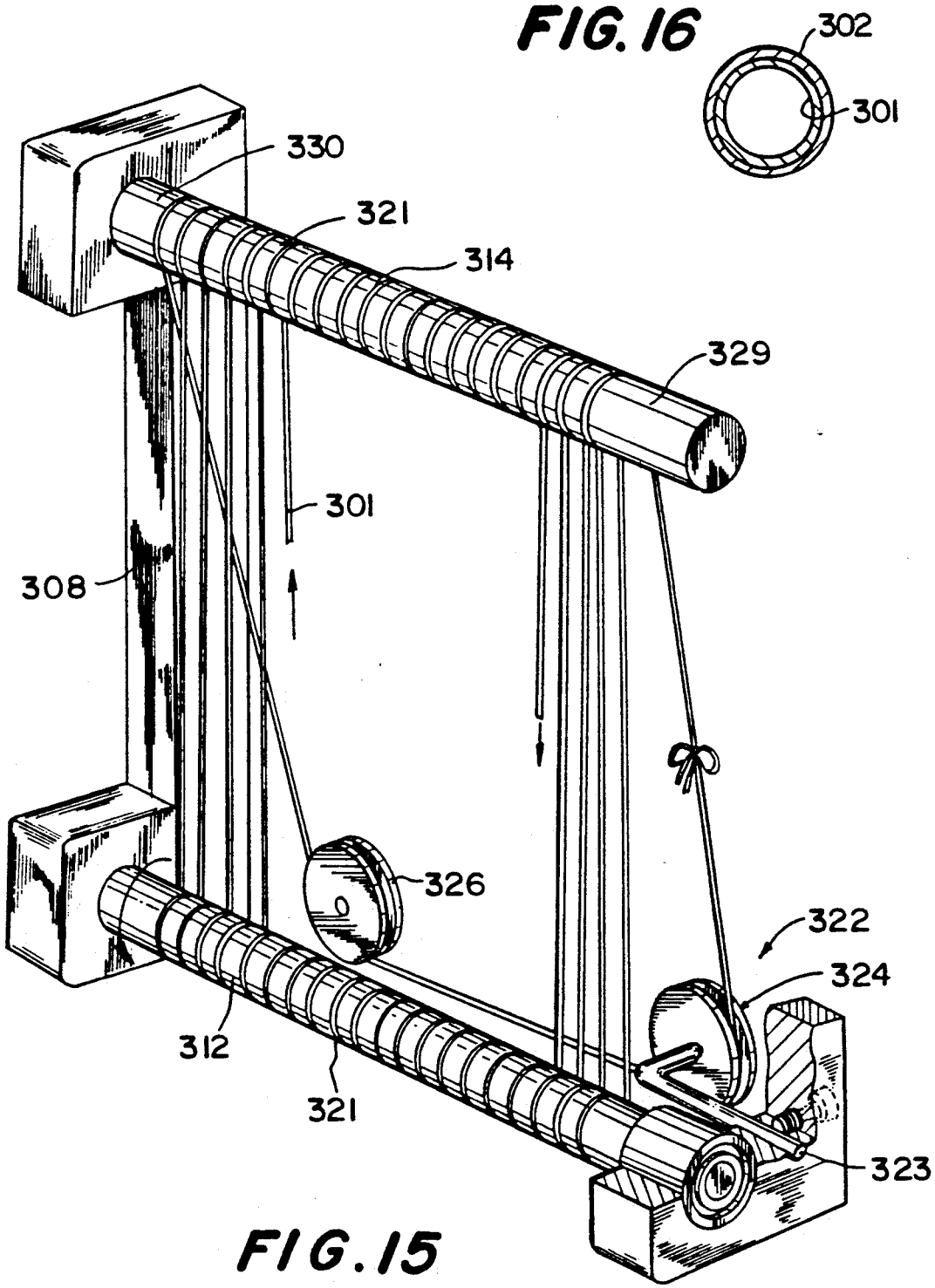
FIG. 15 is an enlarged view of the frame and suture yarn of FIG. 14.
FIG. 16 is a cross sectional view of the coated yarn.

As shown in FIGS. 14, 15 and 16 there is provided a device 300 for coating suture yarn 301 with a uniform, thin and dense adherent film of biocompatible carbon 302 (FIG. 16). The device 300, includes a frame 303 attached to a disk 304 secured by a clamp 306 to the stationary rail 88. The frame 300 includes vertical supports 308 and 310 with transverse rods 312 and 314 therebetween.

The lower rod 312 is rotated by a drive assembly 316 including a rotatable flexible cable 318 connected at one end to the lower rod 312 for rotation thereof, and at the other end to a gear mechanism 320, which, in turn, is rotatably connected to the previously described idler roller 62. As the lower rotatable ring 59 is rotated by the drive roller 60, such rotation is transferred through the idler roller 62, gear mechanism 320 and flexible cable 318 to the lower rod 312.

The rods 312 and 314 include grooves 321 therein for receiving progressive loops of the suture yarn 301 (FIG. 15) as it is rotated by the rod 312. As the rod 312 is so rotated, carbon is sputtered from the target 20, as previously described (FIGS. 1–6), and is deposited on and firmly adheres to the moving yarn 301 to form the biocompatible carbon film 302 (FIG. 16). The grooves 321 are arranged in spaced apart relationship along the rods 312 and 314. As the yarn 301 moves from one groove 321 to another, it is slightly twisted thereby progressively exposing uncoated portions of the yarn to the sputtered carbon.

There also is provided a threading assembly 322, including rotatable pulleys 324 and 326 supported by supports 328 and frame 303.

When the suture yarn 301 comes off the far end 329 of the rod 314 after being coated, it is engaged by the threading assembly 322 and transported to the near end 330 of the bar 314 for further coating as described above. The threading assembly 322 thereby provides means for coating the yarn 301 continuously until the desired coating thickness is obtained.

Following the steps of the described process, suture yarn 301 of DACRON was coated with the biocompatible carbon film 302 of the invention by progressive looping the yarn 301 over the device 300 for about 6.5 hours.

Thus, the present invention includes a wide variety of prosthetic devices, as well as methods of and apparatus for forming such devices. In its broader aspects, the invention is not limited to the specific described embodiments and departures may be made therefrom within the scope of the accompanying claims without departing from the principles of the invention and without sacrificing its chief advantages.

What is claimed is:

1. The method of forming a prosthetic device having a substrate, comprising:
    forming a plasma beam and directing the beam toward a carbon cathode circumscribed by an anode, the cathode and anode being remote from the site of formation of the plasma beam,
    sputtering the carbon cathode by said beam while cooling the cathode and anode and operating the cathode at a high voltage and a low current;
    directing said sputtered carbon onto a substrate at a temperature of below about 250° C. without degradation to form a biocompatible carbon coating firmly adhered on the substrate, and
    operating the method at a pressure of about $10^{-4}$ mbar to about $10^{-2}$ mbar.

2. The method of forming a prosthetic device according to claim 1, wherein the carbon cathode consists of graphite or pyrolytic carbon, and wherein the carbon deposited on the substrate is turbostratic.

3. The method of forming a prosthetic device according to claim 1, wherein the carbon cathode and anode are cooled by water conveyed through conduits contiguous therewith.

4. The method according to claim 1, wherein the substrate is flat and is rotated about the carbon cathode and about itself for uniform distribution of the sputtered carbon thereon.

5. The method according to claim 1, wherein the substrate is tubular and is rotated about its axis for uniform distribution of the sputtered carbon thereon.

6. The method according to claim 1, wherein the substrate is suture yarn and is rotated about a frame for uniform distribution of the sputtered carbon thereon.

7. The method according to claim 1, further comprising masking portions of the substrate so that the sputtered carbon only is deposited on unmasked portions.

8. The method according to claim 1, wherein the substrate is a polyester resin and the temperature at the substrate is maintained at about 80° C. to enhance the adhesion of the sputtered carbon to the substrate.

9. The method according to claim 1, wherein the substrate is polytetrafluoroethylene and the temperature at the substrate is maintained at about 180° C. for about one-sixth of the desired carbon coating thickness, and then at about 40° C. for the balance of the coating of carbon, to thereby enhance the adhesion of the sputtered carbon to the substrate.

10. The method according to claim 1, wherein the carbon sputtered onto the substrate has a thickness of not more than about 1.0 micron.

11. The method according to claim 1, wherein the material of the substrate is selected from the group consisting of polyester resins, polytetrafluoroethylene, silicone, polyacetal resins, polyurethanes, polyethylene, cobalt-chromium alloys, titanium and titanium alloys, and wherein the carbon sputtered on the substrate is turbostratic.

12. The method according to claim 11, wherein the carbon cathode is sputtered in an atmosphere having a pressure of about $10^{-3}$ mbar.

13. Apparatus for depositing a film of biocompatible carbon firmly adherent to a substrate of a prosthetic device, comprising:
    (a) a first chamber for receiving an inert gas;
    (b) means in said first chamber for ionizing the inert gas and issuing a plasma beam therefrom;
    (c) a second chamber open and connected to said first chamber at one end thereof for receiving the plasma beam, and including a carbon cathode positioned at the other end of said second chamber remote from said one end, an annular anode circumscribing said carbon cathode, means about said second chamber for collimating the plasma beam and directing the collimated plasma beam toward said carbon cathode to sputter carbon atoms therefrom, and means mounted in said second chamber for holding a substrate and moving the substrate in the path of the sputtered carbon to form a firmly adherent carbon coating thereon;
    (d) means within and about said second chamber for operating said second chamber at a low pressure;

(e) electrical means connected to said cathode for operating the cathode at a high voltage and low current;

(f) heating means positioned in said second chamber and in proximity of the substrate for heating the substrate to a desired level; and (g) means for cooling the carbon cathode and anode.

14. The apparatus of claim 13, wherein said electrical means comprises an electrical source for maintaining the cathode and anode at a voltage of at least about 500 volts and at a current of not more than about 0.3 amps.

15. The apparatus of claim 13, wherein said means for cooling the carbon cathode and anode comprises:

(a) a first annular conduit contiguous with the outer perimeter of the anode;

(b) a second annular conduit in contact with the carbon cathode; and (c) means for conveying cooling water through said conduits.

16. The apparatus of claim 13 wherein a plurality of substrates are simultaneously coated with sputtered biocompatible carbon, and wherein said means for holding and moving the substrates comprises:

rotatable means mounted at the bottom of the second chamber;

a housing removably mounted on and rotatable with said rotatable means which extends upwardly therefrom and about said carbon cathode, support means for each substrate releasably connected to said housing for holding a substrate thereon during sputtering of the carbon, wherein said support means rotates with said housing about said carbon cathode and is rotatable, at the same time, about its own axis, means connected to said rotatable means for rotation thereof, and means positioned in said second chamber for frictionally engaging each of said support means to effect rotation thereof about its own axis as said housing rotates with said support means about said carbon cathode.

17. The apparatus of claim 16, wherein each of said support means for the substrate comprises:

(a) a disk having a convex rear wall and a concave front wall; and (b) a frame mounted on the concave front wall of said disk for releasably connecting the substrate thereto; and wherein (c) said frictionally engaging means is an annular rail engaged by the bottom of each of said disks.

18. The apparatus of claim 17, wherein said substrates have a flat cross-sectional shape.

19. The apparatus of claim 13 for coating biocompatible carbon on a tubular substrate of a prosthetic device, wherein said holding and moving means for the substrate, comprises:

a rotatable spindle mounted in said second chamber in the path of the sputtered carbon for mounting the tubular substrate thereon, and drive means positioned in said second chamber for rotating said spindle so that sputtered carbon is uniformly deposited on the exposed surface of the rotating tubular substrate.

20. The apparatus of claim 13 for coating biocompatible carbon on a substrate of suture yarn, wherein said holding and moving means for a substrate of suturing yarn comprises:

a frame mounted in said second chamber in the path of the sputtered carbon, including a pair of transversely spaced rods having a plurality of grooves therein for receiving the suture yarn as it is rotated on said rods, wherein said grooves are aligned between rods in such a manner that the yarn turns slightly as it continuously travels from one groove to another therebetween;

means connected to one of said rods for rotation thereof; and means connected to said frame for transferring the suture yarn coming off one end of one of said transverse rods to thereby continuously rotate said suture yarn until it is coated to the desired thickness with firmly adherent biocompatible sputtered carbon.

* * * * *